(12) United States Patent
Guerrero

(10) Patent No.: US 9,669,143 B2
(45) Date of Patent: Jun. 6, 2017

(54) SYNCHRONIZED INTRAVENTRICULAR BALLOON ASSISTANCE DEVICE

(71) Applicant: THE GENERAL HOSPITAL CORPORATION, Boston, MA (US)

(72) Inventor: Jose Luis Guerrero, Norton, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 0 days.

(21) Appl. No.: 14/772,086

(22) PCT Filed: Mar. 3, 2014

(86) PCT No.: PCT/US2014/019841
§ 371 (c)(1),
(2) Date: Sep. 2, 2015

(87) PCT Pub. No.: WO2014/137882
PCT Pub. Date: Sep. 12, 2014

(65) Prior Publication Data
US 2016/0015877 A1 Jan. 21, 2016

Related U.S. Application Data

(60) Provisional application No. 61/772,643, filed on Mar. 5, 2013.

(51) Int. Cl.
*A61N 1/362* (2006.01)
*A61M 1/10* (2006.01)
*A61M 1/12* (2006.01)

(52) U.S. Cl.
CPC ........ *A61M 1/1074* (2014.02); *A61M 1/1008* (2014.02); *A61M 1/1043* (2014.02);
(Continued)

(58) Field of Classification Search
CPC .. A61M 1/1008; A61M 1/101; A61M 1/1024; A61M 1/1034; A61M 1/1043;
(Continued)

(56) References Cited

U.S. PATENT DOCUMENTS 5,765,568 A * 6/1998 Sweezer, Jr. ............ A61M 1/10
128/898
2004/0133062 A1 7/2004 Pai et al.
(Continued)

OTHER PUBLICATIONS

International Search Report and Written Opinion under date of mailing of Jun. 3, 2014 in connection with PCT/US2014/019841.

*Primary Examiner* — George Manuel
(74) *Attorney, Agent, or Firm* — Yakov Sidorin; Quarles & Brady LLP

(57) ABSTRACT

System structured to facilitate a movement of a myocardial wall by pushing such wall with a force originated due to energy harvested by the system from a motion of a ventricular chamber without the use of any external energy. The system includes two pliable storage volumes fluidly interconnected by a passage to form a closed circuit that enables a movement of the fluid from one storage volume to another in response to a user input. Optionally, one of the storage volumes is encased in a cover characterized by a spatially-non-uniform distribution of elastic properties. The method of using the system includes juxtaposition of one of the storage volumes with a ventricular chamber and another of the storage volumes with a targeted myocardial wall to enable reversible flow of fluid within the system during a cardiac cycle.

8 Claims, 7 Drawing Sheets

(52) U.S. Cl.
CPC ............ *A61M 1/122* (2014.02); *A61M 1/101* (2013.01); *A61M 1/1024* (2014.02); *A61M 1/1034* (2014.02); *A61M 1/125* (2014.02); *A61M 2205/0216* (2013.01)

(58) Field of Classification Search
CPC .... A61M 1/1074; A61M 1/122; A61M 1/125; A61M 2205/0216
See application file for complete search history.

(56) References Cited

U.S. PATENT DOCUMENTS

2007/0287880 A1   12/2007   Ovil et al.
2008/0194905 A1   8/2008    Walsh

\* cited by examiner

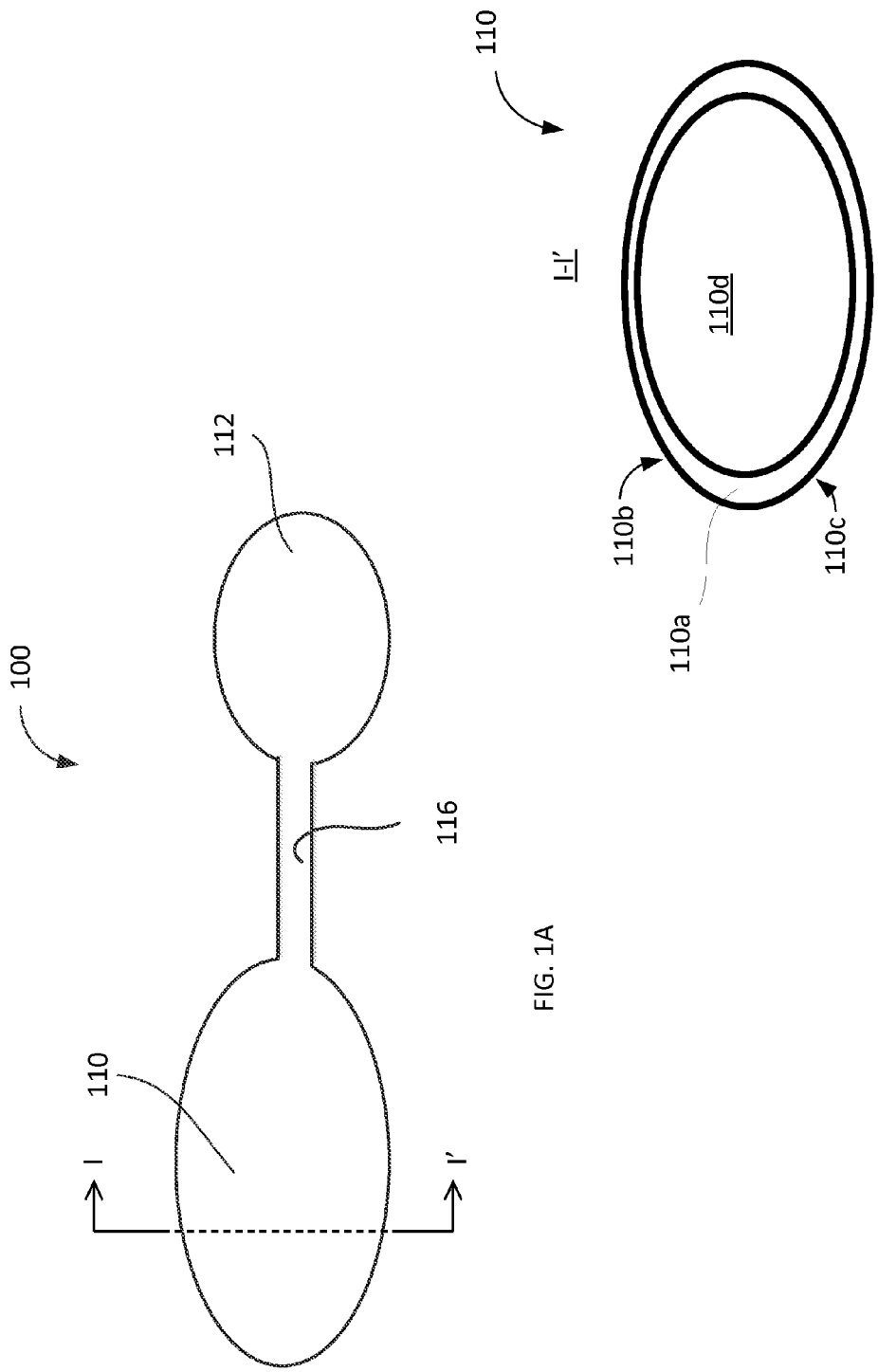

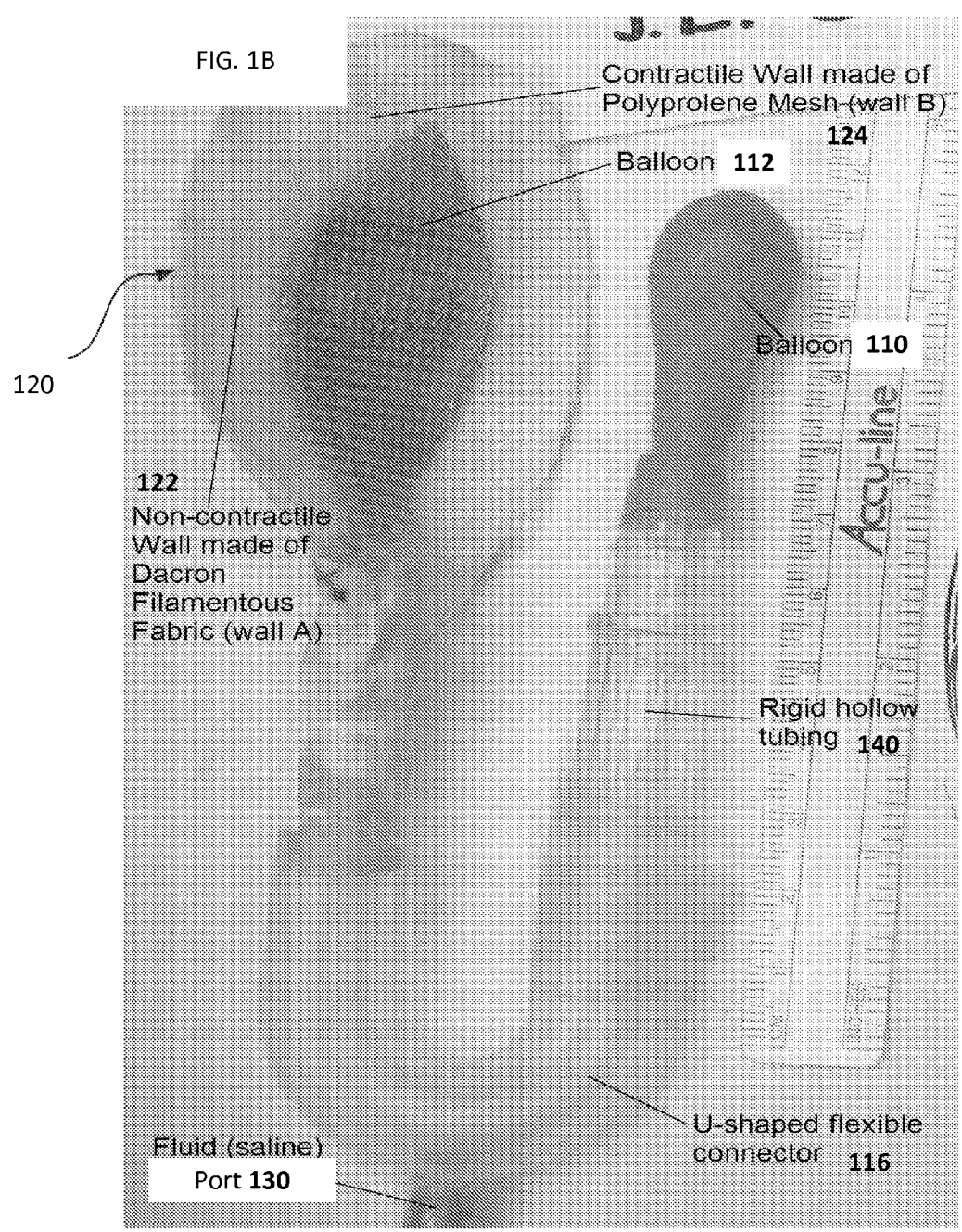

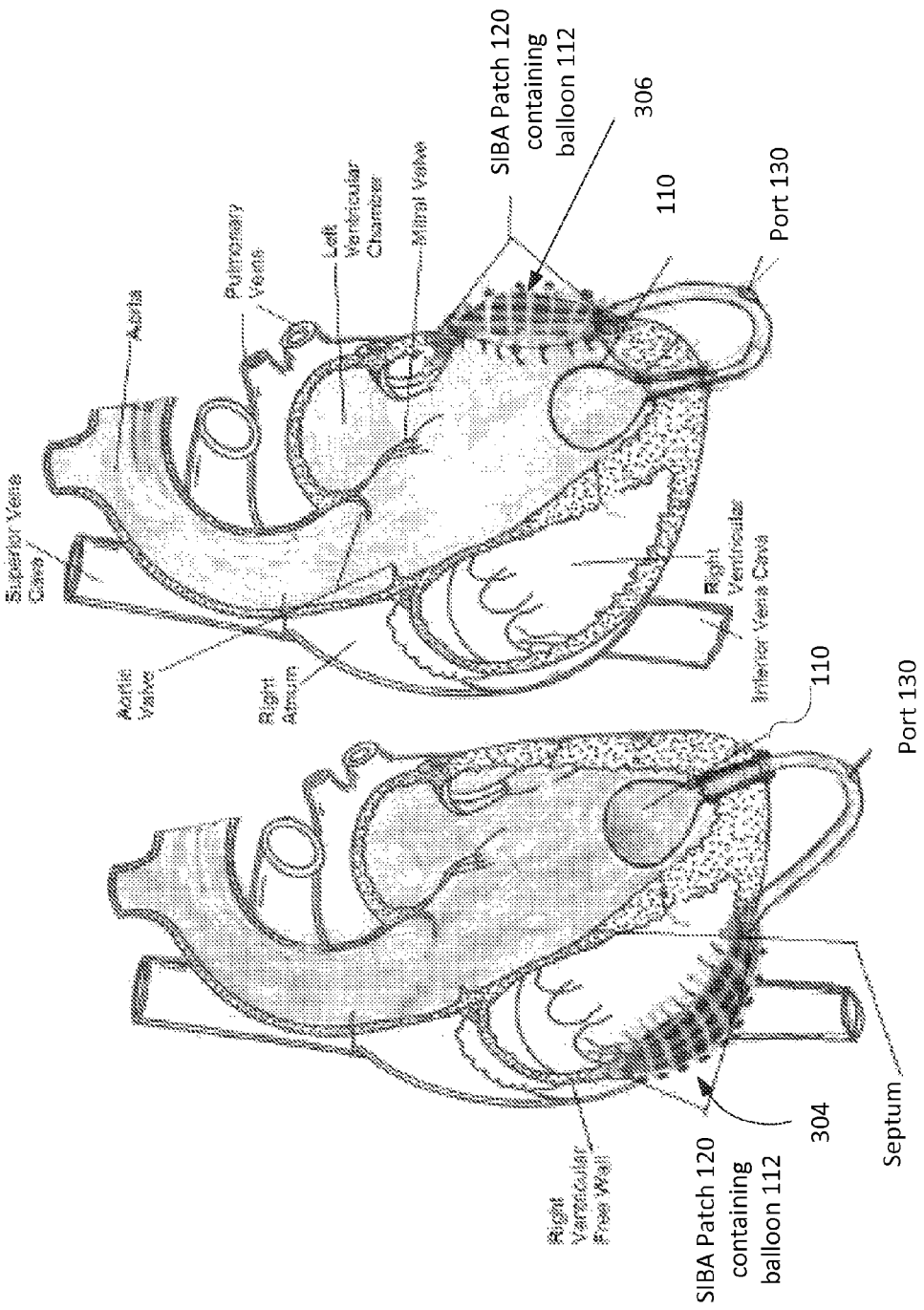

SYNCHRONIZED INTRAVENTRICULAR BALLOON ASSISTANCE DEVICE

CROSS-REFERENCE TO RELATED APPLICATIONS

This present international patent application represents the national stage entry of PCT International Application No. PCT/US2014/019841 filed Mar. 03, 2014, which claims the benefit of U.S. Provisional Patent Application No. 61/772,643 filed on Mar. 05, 2013, the disclosures of which are incorporated by reference here in their entirety for all purposes.

TECHNICAL FIELD

The present invention relates generally to ventricular assistance devices (VADs) and related methods and, more particularly, to a VAD structured to reverse systolic myocardial wall diskinesis.

BACKGROUND

Heart failure caused by Myocardial Infarction is known to have become a serious problem. A term "ventricular assistance device" (VAD) is typically used to refer to a mechanical pump that's used to support heart function and blood flow in people who have weakened hearts. The device takes blood from a lower chamber of the heart and helps pump it to the body and vital organs, just as a healthy heart would.

A VAD has several basic parts. A small tube carries blood out of the heart into a pump. Another tube carries blood from the pump to blood vessels, which deliver the blood to the body tissues. Some VADs pump blood like the heart does, with a pumping action, while other devices exist that keep up a continuous flow of blood. VADs have two basic designs: a transcutaneous VAD (which has its pump and power source located outside of the body) and an implantable VAD with its pump located inside of the body and its power source located outside of the body. In either case, a VAD also normally has a power source connected to a control unit that monitors the VAD's functions. As such, a typical VAD has to be serviced by, for example, replacing batteries, which may require a surgical procedure involving potential hospitalization, anaesthesia, potential infection and other complications.

There remains, therefore, a need for a system and method that facilitate blood circulation with less reliance on external energy.

SUMMARY

Embodiments of the present invention provide a ventricular assistance device (VAD) that includes a tubular element and first and second cavities defined by corresponding first and second walls. The first and second cavities are sealingly cooperated with the tubular element at respective ends of the tubular element such as to establish a closed volume defined by the tubular element and the first and second cavities. The closed volume is filled with fluid at least in part. In a specific implementation, the closed volume defines a closed fluid circuit configured such that the fluid is enabled to flow between the first and second cavities through the tubular element in response to a user input applied to a cavity. In a related embodiment, the VAD may additionally include a smooth sac enclosing the second cavity, the sac having compliant and non-compliant sides characterized in that the compliant side is more ductile than the non-compliant side.

Embodiments additionally provide a method for facilitating a movement of a myocardial wall, which method includes (i) transferring a motion of a ventricular chamber to a first balloon containing a liquid and disposed in the ventricular chamber; (ii) in response to the transferred motion, forming a flow of the fluid from the first balloon through a tubular connector to a second balloon juxtaposed with the myocardial wall; and (iii) transferring motion of the second balloon defined by the flow of fluid to the myocardial wall. The transferring motion of the second balloon to the myocardial wall may include changing geometry of the second balloon such as to apply a force to the myocardial wall. Alternatively or in addition, the step of transferring motion of the second balloon to the myocardial wall may include transferring motion from the second balloon through a layer of material separating the second balloon from the myocardial wall.

BRIEF DESCRIPTION OF THE DRAWINGS

The invention will be more fully understood by referring to the following Detailed Description in conjunction with the Drawings (that are generally not to scale), of which:

FIG. 1A is a diagraph illustrating schematically a component of the embodiment of the invention;

FIG. 1B is an illustration of an embodiment;

FIG. 1C is a cross-section of an element of the embodiment of FIG. 1A;

FIG. 3A illustrates schematically positioning of the embodiment in cooperation the left ventricle chamber and the right ventricular free wall;

FIG. 3B illustrates schematically positioning of the embodiment in cooperation with the left ventricular chamber and the infarcted area of the posterior wall;

DETAILED DESCRIPTION

Figure 2A:
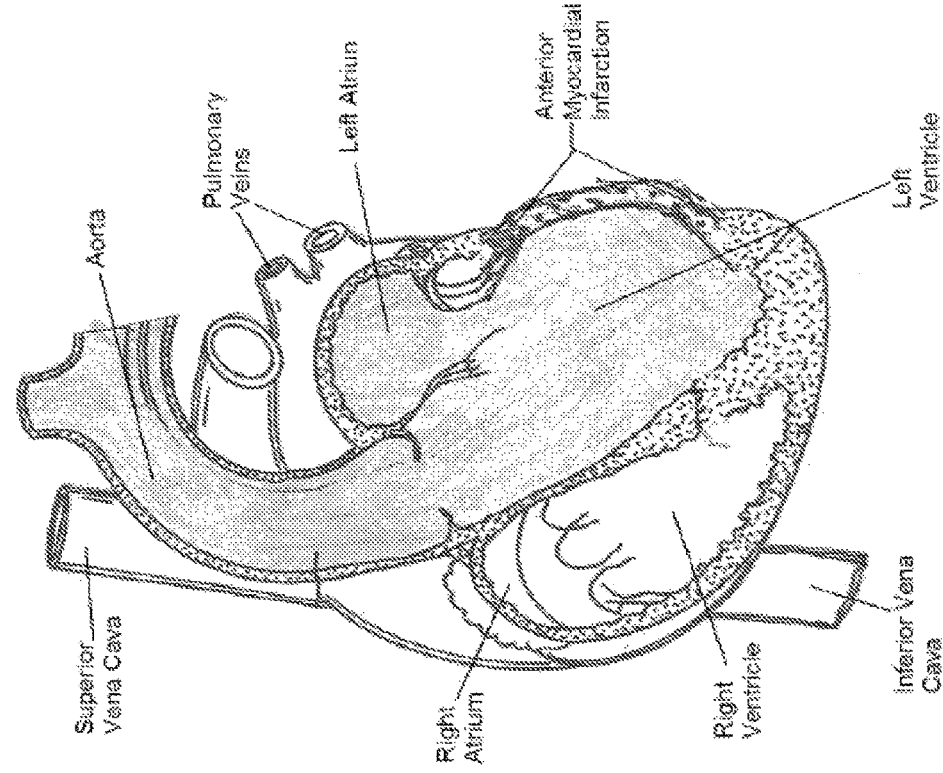
FIGS. 2A and 2B illustrate schematically right and left ventricular infarction of the anterior myocardial wall.

While surgical approaches to repair other forms of mitral valve disease have recently improved, treating valve leakage of the tricuspid and mitral valves continues to be a problem. Patient and animal studies have shown that the current standard treatment, reduction of annular size, often fails because leaflet tethering in the posterior papillary muscle persists. Patients also frequently present with ischemic MR despite afterload reduction therapy, which may not be able to overcome irreversible remodeling.

The present application discloses a device and method enabling a transformation of physiological excitation into a motion for harvesting and transferring energy to restore normal motion of infarcted myocardium. As such, embodiments of the present invention facilitate improvement in ventricular performance and reversal of valve leakage following a myocardic infarction. Device and method of the invention can be also employed to treat Ischemic Mitral Regurgitation (MR), Tricuspid Regurgitation (TR), and Right Ventricular Free Wall Abnormalities. The device can be beneficially used in patients with atrial fibrillation (due to atrial dilation) by providing active mechanical contraction.

In particular, a system of the invention is structured to facilitate a movement of a myocardial wall by pushing such wall with a force originated due to energy harvested by the system from a motion of a ventricular chamber without the use of any external energy. The system includes two pliable storage volumes fluidly interconnected by a passage to form a closed circuit that enables a movement of the fluid from one storage volume to another in response to a user input. Optionally, one of the storage volumes is encased in a cover characterized by a spatially-non-uniform distribution of elastic properties. The method of using the system includes juxtaposition of one of the storage volumes with a ventricular chamber and another of the storage volumes with a targeted myocardial wall to enable reversible flow of fluid within the system during a cardiac cycle.

In reference to FIGS. 1A and 1B, an embodiment 100 of the device (referred to herein as SIBA device) includes two balloons 110, 112 made of appropriate flexible, elastic biocompatible material and filled with fluid (for example, liquid or gas) and fluidly (for example, liquidly, gaseously) interconnected with a hollow tube 116. In one implementation, the device 100 includes a saline-filled closed circuit with balloon 110 attached to each end of the tube 116 that is preferably non-compliant, in that it does not substantially stretch in response to the internal fluid pressure to not affect the flow of fluid inside the tube. The tube 116 may have the length between about 6 and about 10 cm. The balloon 112 is made of a less-elastic material and is structured to have larger surface area (as compared to the balloon 110). In operation, the device 100 is extended between the ventricular chamber (housing the first of the two balloons, for example balloon 110) and the epicardial surface of the ischemic myocardium (with which the second balloon 112, housed in a patch 120 (shown later in FIGS. 1B, 2A, 2B, 3A, 3B) having compliant and non-compliant sides, is in contact through the compliant side of the patch). The terms "compliant" and "non-compliant" are used relatively to one another to describe an ability of the material of the patch to stretch.

Examples of a fluid filling the circuit 100 include saline, fluorocarbon liquids, and $CO_2$. Carbon dioxide ($CO_2$) gas, for example, can be used as a contrast agent in the venous circulation: a bolus intravenous injection of $CO_2$ in quantities of 100 to 200 cc were shown to cause no significant changes in vital signs. When $CO_2$ is injected into the blood, it is combined with water to produce carbonic acid. It becomes bicarbonate ($HCO3-$) in the blood stream; bicarbonate reverts to $CO2$ before being expelled out of capillaries into the lung. Carbonic anhydrase catalyzes the conversion of $CO2$ to bicarbonate and protons. $CO2$ is eliminated by the lungs in a single pass.

FIG. 1B demonstrates a practical implementation of the device 100. The patch 120 housing the balloon 112 is structured to be a smooth sack. The non-compliant portion 122 (shown as a wall A) of the patch 120 is made from, for example, Dacron Filamentorus fabric (by Bard Peripheral Vascular Inc.), while the compliant portion 124 (shown as a wall B) of the patch 120 is structured, for example, as a non-absorbable polyprolene mesh (by Ethicon). The non-compliant and compliant portions of the patch are attached to each other (for example, with silicon adhesive such as adhesive from the RTV series) to create a cavity therebetween dimensioned to house and embrace the balloon 112. The surface area of the compliant portion of the patch (which may be structured as a mesh) is larger than the surface area of the non-compliant portion, thereby allowing the balloon 112 to expand with preference towards the compliant portion of the patch during the transmission of fluid between the balloons 110, 112. As the patch is oriented with its compliant side towards the myocardium wall in question, such preferential expansion of the balloon 112 is directed to the myocardial wall.

In further reference to FIG. 1B, the tube 116 is shown to be U-shaped and equipped with a fluid port 130 disposed or located between the ends of the tube 116, for (re)-filling of the SIBA device 110 with the chosen internal fluid. Optionally, the flexible tube 116 is connected to the balloon 110 via a secondary tubing portion 140. FIG. 1C illustrates a structure of an individual balloon of the embodiment 100 (such as the balloon 110, for example) in a cross-sectional view along the plane I-I' indicated in FIG. 1A. An individual balloon 110 of then system 100 includes a flexible and stretchable wall 110a limited by inner and outer surface 110b, 100c that define internal volume of the balloon 110 filled with fluid as discussed above.

According to an implementation of the invention, the motion associated with the pressure created by the contraction of the ventricular chamber creates a pressure on the first balloon causing the liquid to flow through the tube from the first balloon to the second balloon. As the expanding second balloon is situated in contact with the injured wall of myocardium, it exerts pressure on the wall facilitation the restoration of the wall's motion and repositioning the papillary muscles. In a related implementation, the transfer of energy of motion of the ventricular chamber to the infarcted area not only restores the systolic wall motion and increases ejection fraction, but also reverses ischemic mitral and tricuspid valve regurgitation by repositioning the papillary muscles.

Figure 2B:
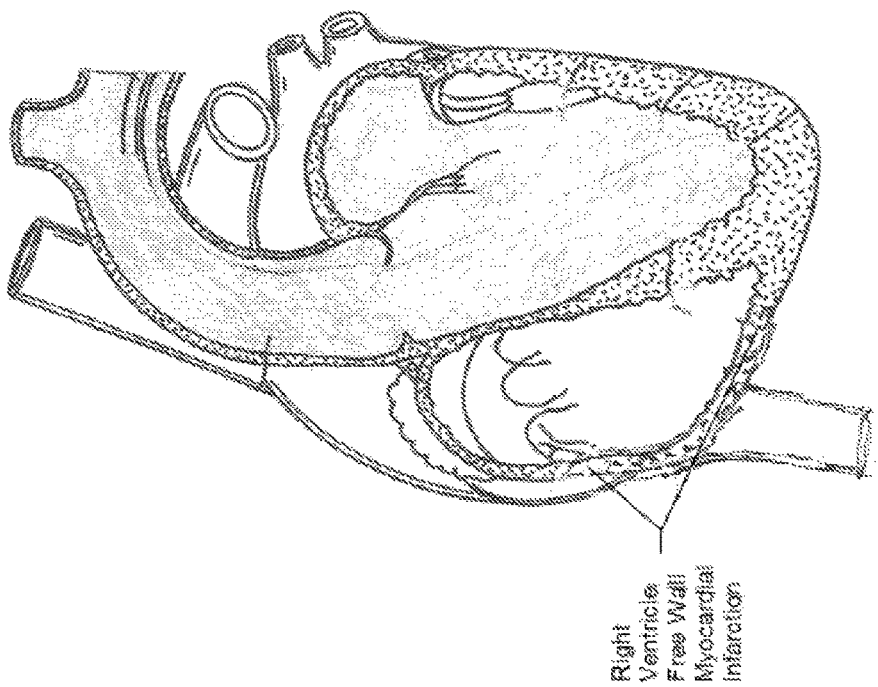

Two principal embodiments of the device of the invention include structures done under middle sternotomy or left thoracotomy. FIGS. 2A and 2B illustrate schematically right and left ventricular infarction of the anterior myocardial wall, where one of the balloons of the device is disposed in a myocardial chamber through the apex of the chamber. FIG. 3A illustrates schematically the SIBA device 100 with the balloon 110 in the left ventricle chamber and the balloon 112 that is housed in the patch 120 attached to the infarcted area on the right ventricular free wall 304. Such implementation can also provide benefits to patients with high pulmonary pressure. FIG. 3B depicts the device 110 oriented with the balloon 110 in the left ventricular chamber, while the balloon 112 is housed in the patch 120 juxtaposed to the infarcted area of the wall 306, facilitating the restoration of systolic wall motion in operation. In either implementation, the force generated by the left ventricle upon contraction is transferred, through the flow of fluid from the balloon 110 through the connecting tube 116 through the expansion of the balloon 112, to a wall adjoining the patch 120 thereby facilitating the motion of the wall and increasing cardiac output.

Figure 4A:
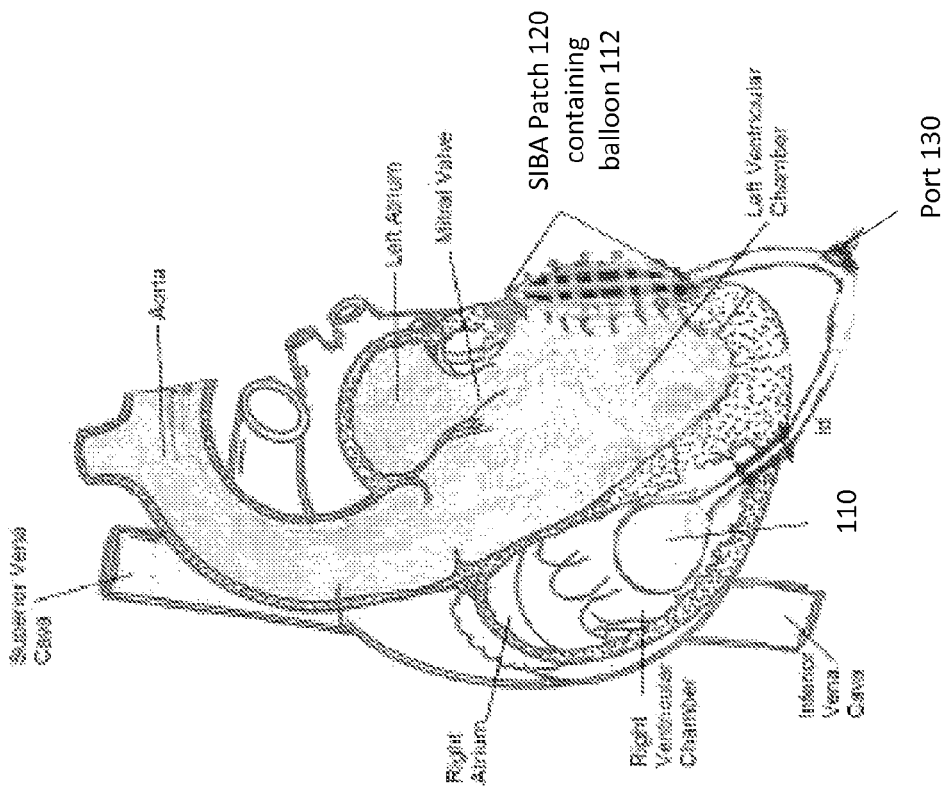
FIG. 4A illustrates the placement of the first balloon of the embodiment in the right ventricular cavity and the positioning of the second balloon of the embodiment in juxtaposition with the infarcted area of the right ventricular free wall.
Figure 4B:
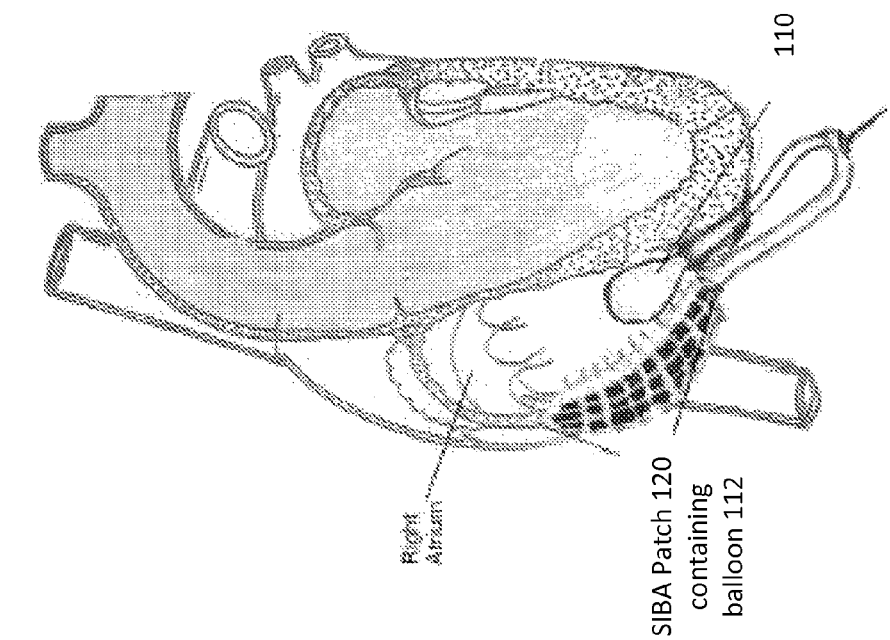
FIG. 4B illustrates the placement of the first balloon of the embodiment in the right ventricular cavity and the second balloon of the embodiment in cooperation with to the infarcted area that includes the anterior papillary muscle.

FIG. 4A illustrates the placement of the balloon 110 of the SIBA device 100 in the right ventricular cavity and the positioning of the balloon 112 such that the patch 120 housing the balloon 112 is juxtaposed with the infarcted area of the right ventricular free wall 304. The fluid pressure generated in the balloon 110 by the motion of the right ventricular chamber is transferred along the tube 116 towards the balloon 112 and onto the right ventricular free wall 304 thereby restoring systolic wall motion of the infarcted area and increasing the cardiac output. FIG. 4B illustrates a specific case in which the balloon 110, placed in the right ventricular cavity, can provide some assistance to the balloon 112 and the patch 120 attached to the infarcted area that includes the anterior papillary muscle, thereby reducing Mitral Regurgitation.

In one implementation, the compliant side of the SIBA patch 120 is affixed (for example, sewn) internally onto the myocardium over the region of infraction using several (for example, eight) interrupted Ethibond Excel non-absorbable sutures formed along the edges of the patch 120. The balloon 110 is placed into a ventricle cavity at its apex.

In further reference to FIGS. 3A, 3B, 4A, and 4B, prior to the implantation of the balloon 110 of the device into a ventricular chamber, a mattress suture will be placed around the apex of the chamber. An embodiment of the device of the invention can be implanted, for example, via open heart surgery with techniques similar to those used for implantation of traditional VAD devices. Alternatively, the device can be implanted with a catheter mechanism through vessels such as a hollow tubular element without the need for major open heart surgery. In one implementation, the balloon 100 is first inserted into the shaft 116, attached to the balloon, by suction. With a blade, a puncture is made into the apex of the chamber in question and the shaft (with circumference of about 8 mm) containing the balloon 110 is inserted into the ventricular chamber. The balloon 112 is placed on the epicardium surface of the infarcted area with several (for example, eight) single stitches applied to the border zone of the infarcted area. Both balloons 110, 112 are later inflated during the procedure of filling the circuit 110 with appropriate fluid through the port 116. The port 116, made of selastic material, automatically seals upon the withdrawal of a needle used to inject fluid into the circuit 100.

To test the performance of an embodiment of the system, in a practical study MR was created occurring in acute and chronic ischemia. Ligating certain left circumflex coronary artery branches reproduces acute MR with segmental ischemia. These models produce ischemia of the inferior papillary muscle, creating MR by preventing mitral leaflet coaptation. The same hold true for right ventricular failure caused by an infarction of the right ventricular free wall due to occlusion of the right coronary artery that leads to severe tricuspid regurgitation decreasing stroke volume. The normal right ventricle has the same stroke volume as the left ventricle, but with much less stroke work due to the low resistance of the pulmonary vasculature. During right ventricular failure caused by high pulmonary pressure or right ventricular infarction, the increased size and pressure overload to the right ventricle produces diastolic dysfunction of the left ventricle (LV).

The empirical data, listed below and acquired in three tests performed in three animals with the use cardiac of ultrasound measurements, demonstrate that while the device is working compared with in place, but not working, ejection fraction, contractility, and cardiac output increase in three animals by 43%, 26%, and 12% respectively.

Studies were performed on animals 60+ days post-myocardial infarction of the inferior wall including the papillary muscle.

SIBA Device 1, #0040.
BASELINE: BALLOON EMPTY: post-SIBA device placement, 120 days post-MI.
Echo Data:
HR: 82 bpm
EDV: 75 ml
ESV: 46.1 ml
EF: 38.5%
SV: 28.9 ml
CO: 2369.8
BALLOON FULL: SIBA device working, 120 days post-MI
Echo Data:
HR: 85 bpm
ESV: 36.2 ml
EF: 46.5%
SV: 31.2 ml/min
CO: 2558.4
percent change cardiac output: 11.91%; percent change stroke volume: 7.96%
SIBA Device 2, #2004
BASELINE: 60 days post-MI, BALLOON EMPTY: post-SIBA device placement
Echo Data:
HR: 88 bpm
EDV: 71.1 ml
ESV: 42 ml
EF: 29.1%
stroke vol: 31 ml
CO: 2728
BALLOON FULL: SIBA device working, 60 days post-MI
Echo Data:
HR: 93 bpm
EDV: 89 ml
ESV: 52 ml
EF: 37%
stroke vol: 42 ml
CO: 3906
percent change cardiac output: 42.86%; percent change stroke volume: 35.48%
SIBA Device 3, #2072
BASELINE: 60 days post-MI, BALLOON EMPTY: post-SIBA device placement
Echo Data
HR: 91.6 bpm
EdVol: 114 ml
EsVol: 73 ml
EF: 42%
Svl: 46 ml
CO: 4.2 L/min
BALLOON FULL: SIBA device working, 60 days post-MI
Echo Data
HR: 92.3 bpm
EdV: 117
EsVol: 67 ml
EF 43.4%
SV: 57 ml
CO: 5.3 L/min
percent change cardiac output: 26.19%; percent change stroke volume: 23.91%

In accordance with specific embodiments described with reference to Figures, a system and method are provided for using the body's internal energy from movements of a ventricular chamber. An energy collector cooperated with the heart absorbs energy and is deformed, at its first end, from a physiological force or motion associated with an input displacement of the chamber during the systolic portion of the cardiac cycle. The first end of the energy collector then transfers the absorbed energy through the motion of fluid in a closed circuit connecting the ends of the collector towards its second end, where it releases the transferred energy to allow the second end of the energy collector to move preferentially towards the identified portion of the wall of myocardium and pass on its output displacement to such identified portion. The energy collector is not coupled to any device external to the collector such as a power converter, for example. During the diastolic portion of the cardiac cycle, the myocardial wall against which the second end of the energy-collector is positioned to lean transfers at least a portion of its motion to the second end, generating a force directing a flow of fluid from inside the second end towards the first end, thereby substantially completing the cycle of fluid oscillation inside the circuit of the energy collector.

Figure 5:
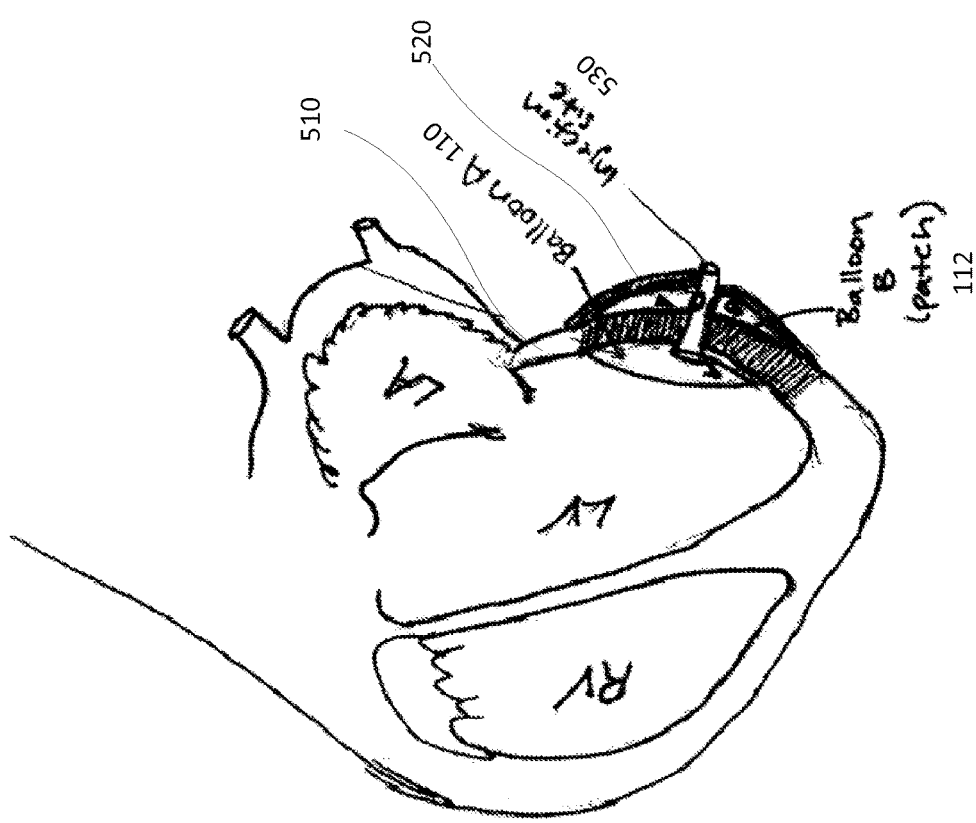
FIG. 5 illustrates an alternative embodiment of the device and method of using the same.

Modifications to, and variations of, the illustrated embodiments may be made without departing from the inventive concepts disclosed herein. For example, FIG. 5 provides a schematic illustration of a modified embodiment of the device, shown to be juxtaposed with the myocardium such that the balloon 110 is structured to sit substantially flat against the infarcted myocardium wall 510, and the fluid between the balloons 110, 112 is transferred through a short tube 516 sealingly affixed to an opening in the central portion of the balloon 110 and having at least one opening 520 in a wall of the tube 516 that fluidly connects the hollow of the tube 516 and the volume inside the balloon 112. The injection site 530 proximate an end of the tube 516 can be used to add/remove the fluid into the balloon-based circuit. In comparison with the embodiment 100 of FIG. 1A, for example, the embodiment of FIG. 5 may require less fluid for operation and a shorter tube (about 3-4 cm in length).

In further reference to FIG. 5, the balloon 110 is inserted through the center of the infarcted area using a mattress suture, in a fashion similar to that described above in reference to FIGS. 3A through 4B. In comparison, however, the insertion of the balloon 110 in the embodiment of FIG. 5 requires a smaller puncture due to the fact that the shaft used is a shaft with a 4 mm circumference and the length about 3.5 cm.

Figure 6:
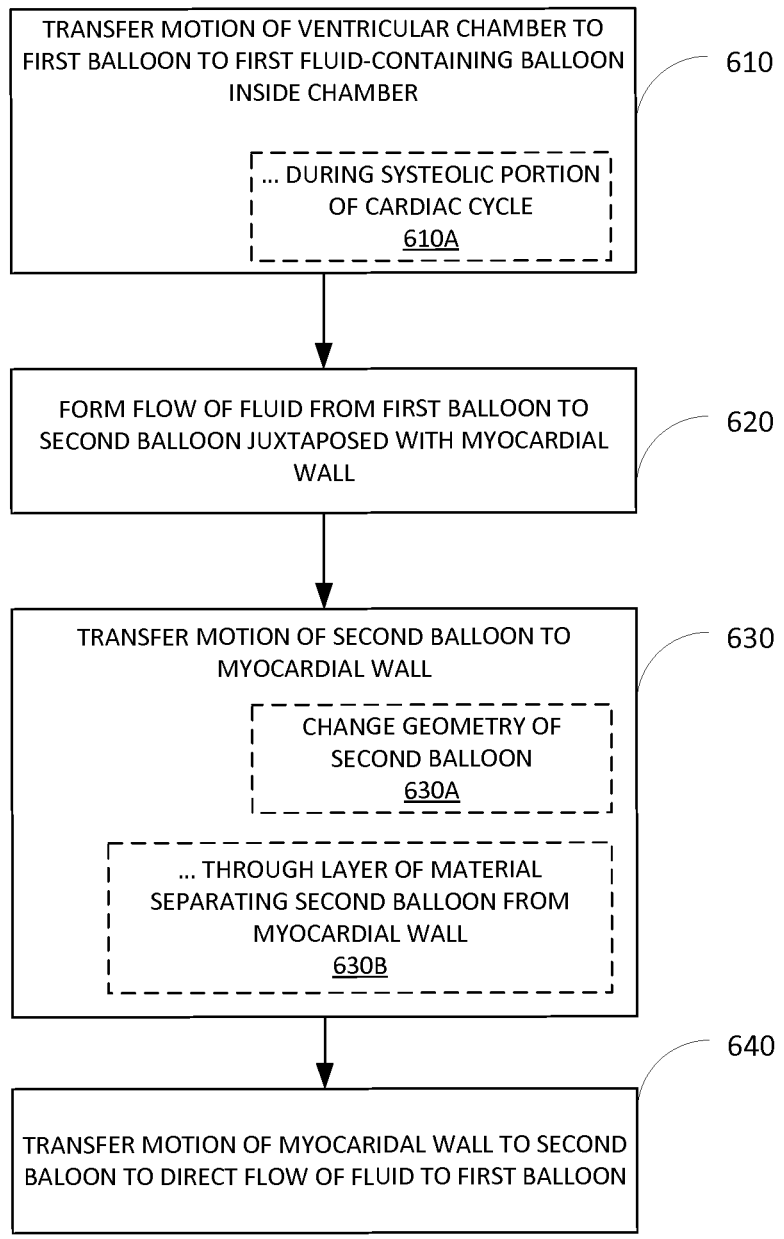
FIG. 6 provides a flow-chart illustrating an example of the method of the invention.

An example of a method of the invention for facilitating a movement of a myocardial wall is schematically illustrated in FIG. 6. As shown, at step 610, energy of the ventricular chamber is transferred (during the motion of the ventricular chamber) to a first fluid-containing balloon (that has been disposed in that chamber as part of the device containing the interconnected first and second balloons, as discussed above). A flow of the fluid from the first balloon to a second balloon (that has been juxtaposed with the myocardial wall) through a connector between the two balloons is effectuated, in response to the transfer of motion, at step 620. Step 630 indicates a further process of transferring motion of the second balloon (defined by said flow of fluid) to the myocardial wall). Moreover, the method may further include a step 640, at which energy of the myocardial wall is transferred through the motion of the myocardial wall to the second balloon during a diastolic portion of the cardiac cycle to direct a flow of the fluid in reverse, from the second balloon to the first balloon.

It is appreciated that the process of step 610 may include a process of transferring a motion of a ventricular chamber during a systolic portion of a cardiac cycle, as shown by 610A. It is also appreciated that the process of transfer of motion at step 630 may include changing geometry of the second balloon (as shown by 630A). Alternatively or in addition, the process of transfer of motion at step 630 may be effectuated through a layer of material separating the second balloon from the myocardial wall (as shown by 630B), the presence of which layer in the proximity of the myocardial wall was optionally established during the installation of the device.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, when the present disclosure describes features of the invention with reference to corresponding generally-not-to-scale drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, the depicted order and steps depicted therein may be indicative of only one embodiment of the presented method, and other steps and methods may be conceived. Without loss of generality, the order in which processing steps or particular methods occur may or may not strictly adhere to the order of the corresponding steps shown.

The invention as recited in claims appended to this disclosure is intended to be assessed in light of the disclosure as a whole, including features disclosed in prior art to which reference is made.

Furthermore, disclosed aspects, or portions of these aspects, may be combined in ways not listed above. Accordingly, the invention should not be viewed as being limited to the disclosed embodiment(s).

What is claimed is:

1. A method for facilitating a movement of a myocardial wall, the method comprising:

transferring a motion of a ventricular chamber to a first balloon disposed there within, the first balloon containing a fluid;

in response to the transferred motion, forming a flow of the fluid from the first balloon through a tubular connector to a second balloon juxtaposed with the myocardial wall;

transferring motion of the second balloon defined by the flow of fluid to the myocardial wall.

2. A method according to claim 1, wherein the transferring motion of the second balloon includes changing geometry of the second balloon to apply a force to the myocardial wall.

3. A method according to claim 2, wherein the transferring motion of the second balloon includes transferring motion from the second balloon through a layer of material separating the second balloon from the myocardial wall.

4. A method according to claim 1, wherein the transferring a motion of a ventricular chamber includes transferring a motion of a ventricular chamber during a systolic portion of a cardiac cycle.

5. A method according to claim 1, further comprising: during a diastolic portion of a cardiac cycle, transferring a motion of the myocardial wall to the second balloon to direct a flow of the fluid from the second balloon to the first balloon.

6. A ventricular assistance device (VAD) comprising:

a tubular element;

first and second elastic cavities defined by corresponding first and second walls, the first and second cavities being sealingly cooperated with the tubular element at respective ends thereof to establish a closed volume defined by the tubular element and the first and second cavities;

a smooth sac enclosing the second cavity, the sac having compliant and non-compliant sides characterized in that the compliant side is more ductile than the non-compliant side; and a fluid port in the tubular element, the port providing access to the closed volume.

7. A VAD according to claim 6, wherein the closed volume defines a closed fluid circuit configured such that fluid, delivered to the closed volume, is enabled to flow between the first and second cavities through the tubular element in response to a user input applied to a cavity.

8. A VAD according to claim 6, wherein the closed volume contains fluid.

* * * * *